United States Patent [19]

Janssens et al.

[11] Patent Number: 4,835,161

[45] Date of Patent: May 30, 1989

[54] ANTI-HISTAMINIC COMPOSITIONS CONTAINING N-HETEROCYCLYL-4-PIPERIDINAMINES

[75] Inventors: Frans E. Janssens, Bonheiden; Jozef F. Hens, Nijlen; Joseph L. G. Torremans, Beerse, Jozef J. P. Heykants, Vosselaar, all of Belgium

[73] Assignee: Janssen Pharmaceutica N.V., Beerse, Belgium

[21] Appl. No.: 5,546

[22] Filed: Jan. 21, 1987

Related U.S. Application Data

[63] Continuation-in-part of Ser. No. 825,491, Feb. 2, 1986, abandoned.

[51] Int. Cl.⁴ ............... A61K 31/44; C07D 401/00

[52] U.S. Cl. ............... 514/303; 514/255; 514/313; 514/322; 544/127; 544/139; 546/118; 546/194; 546/199

[58] Field of Search ............. 514/287, 255, 313; 564/303; 546/199

[56] References Cited

U.S. PATENT DOCUMENTS 4,219,559  8/1980  Janssens et al. .............. 514/227
4,556,660  12/1985  Janssens et al. .............. 514/272

*Primary Examiner*—Leonard Schenkman

[57] ABSTRACT

Anti-allergic compositions containing one or more pharmaceutical carriers and as active ingredient at least one compound which is a N-heterocyclyl-4-piperidinamine and methods of treating allergic diseases in warm-blooded animals. Novel N-heterocyclyl-4-piperidinamines.

19 Claims, No Drawings

ANTI-HISTAMINIC COMPOSITIONS CONTAINING N-HETEROCYCLYL-4-PIPERIDINAMINES

REFERENCE TO RELATED APPLICATION

This application is a continuation-in-part of our prior application Ser. No. 825,491, filed Feb. 2, 1986, now abandoned.

BACKGROUND OF THE INVENTION

In U.S. Pat. No. 4,219,559 there are described a number of 1-substituted N-heterocyclyl-4-piperidinamines as compounds having useful anti-histaminic properties. The same reference also teaches the use of a number of N-heterocyclyl-4-piperidinamines having a piperidine moiety which is either unsubstituted in the 1-position or substituted with an alkyloxycarbonyl or phenylmethoxycarbonyl group, as useful intermediates. A number of these compounds are further described in more detail in J. Med. Chem. 1985, 28, pp. 1925–1933, 1934–1943 and 1943–1947. Furthermore, in J. Med. Chem. 1985, 28, 1934–1943 there are described the synthesis and anti-histaminic properties of the compound 1-[(4-fluorophenyl)methyl]-4-(4-piperidinyl)-1H-benzimidazol-2-amine dihydrobromide. The latter compound is taught in "Astemizole: a New, Non-sedative, Long-acting $H_1$-antagonist, Med. Publ. Found. Symp. Ser. 84, 25–34 (1984)" to be an active metabolite of astemizole.

In U.S. Pat. No. 4,556,660 and in the Published Eur. Pat. Appl. Nos. 145 037, 144 101 and 151 824 there are described further series of N-heterocyclyl-4-piperidinamines having a 1-substituted piperidine moiety as compounds having useful anti-histaminic and serotonin-antagonistic properties, while N-heterocyclic-4-piperidinamines being unsubstituted in the 1-position of the piperidine moiety are described as intermediates.

Finally, in the published Eur. Pat. Appl. No. 151,826 there are described a number of 4-(bicyclic heterocyclyl)methyl and -heteropiperidines having useful anti-histaminic and serotonin-antagonistic properties.

The present invention concerns compositions containing the previously-mentioned N-heterocyclyl-4-piperidinamines bearing either a hydrogen atom, an alkyloxycarbonyl or phenylmethoxycarbonyl group in the 1-position of the piperidine moiety as active ingredients and methods of treating allergic diseases based on the use of the said compositions.

DESCRIPTION OF THE INVENTION

The present invention is concerned with anti-allergic compositions comprising one or more pharmaceutically acceptable inert carriers and as active ingredient an anti-allergic effective amount of at least one compound having the formula the pharmaceutically acceptable acid addition salts and the stereochemically isomeric forms thereof, wherein L is hydrogen, $C_{1-6}$alkyloxycarbonyl or phenylmethoxycarbonyl;

$A^1=A^2-A^3=A^4$ is a bivalent radical having the formula

| | |
|---|---|
| —CH=CH—CH=CH— | (a), |
| —N=CH—CH=CH— | (b), |
| —CH=N—CH=CH— | (c), |
| —CH=CH—N=CH— | (d), |
| or | |
| —CH=CH—CH=N— | (e), | wherein one or two hydrogen atoms in said radicals (a)–(e) may, each independently from each other, be replaced by halo, $C_{1-6}$ alkyl, $C_{1-6}$ alkyloxy, trifluoromethyl or hydroxy;

R is a member selected from the group consisting of hydrogen and $C_{1-6}$ alkyl;

$R^1$ is a member selected from the group consisting of hydrogen, $C_{1-10}$ alkyl, $C_{3-6}$ cycloalkyl, $Ar^1$ and $C_{1-6}$ alkyl substituted with one or two $Ar^1$ radicals;

$R^2$ is a member selected from the group consisting of hydrogen, $C_{1-6}$ alkyl, $C_{3-6}$ cycloalkyl, ($C_{1-6}$ alkyl)—CO—, ($C_{1-6}$ alkyloxy)—CO and $Ar^2$-$C_{1-6}$ alkyl;

wherein $Ar^1$ is a member selected from the group consisting of phenyl, being optionally substituted with up to three substituents each independently selected from the group consisting of halo, hydroxy, nitro, cyano, trifluoromethyl, $C_{1-6}$ alkyl, $C_{1-6}$ alkyloxy, $C_{1-6}$ alkylthio, mercapto, amino, mono- and di($C_{1-6}$ alkyl)amino, carboxyl, $C_{1-6}$ alkyloxycarbonyl and $C_{1-6}$ alkyl—CO—; thienyl; halothienyl; furanyl; $C_{1-6}$ alkyl substituted furanyl; pyridinyl; pyrazinyl; thiazolyl and imidazolyl optionally substituted with $C_{1-6}$ alkyl; and wherein $Ar^2$ is a member selected from the group consisting of phenyl being optionally substituted with up to three substituents each independently selected from the group consisting of halo, hydroxy, nitro, cyano, trifluoromethyl, $C_{1-6}$ alkyl, $C_{1-6}$ alkyloxy, $C_{1-6}$ alkylthio, mercapto, amino, mono- and di($C_{1-6}$ alkyl)amino, carboxyl, $C_{1-6}$ alkyloxycarbonyl and ($C_{1-6}$ alkyl)—CO.

As used in the foregoing definitions the term halo is generic to fluoro, chloro, bromo and iodo; the term "$C_{1-6}$ alkyl" is meant to include straight and branch chained saturated hydrocarbon radicals having from 1 to 6 carbon atoms such as, for example, methyl, ethyl, 1-methylethyl, 1,1-dimethylethyl, propyl, 2-methylpropyl, butyl, pentyl, hexyl and the like; "$C_{1-10}$ alkyl" is meant to include $C_{1-6}$ alkyl radicals, as defined hereinabove, and the higher homologs thereof having from 7 to 10 carbon atoms; the term "$C_{3-6}$ cycloalkyl" is generic to cyclopropyl, cyclobutyl, cyclopentyl and cyclohexyl.

Preferred compounds of formula (I) to be used as active ingredient in the compositions of the present invention are those wherein $A^1=A^2-A^3=A^4$ is a bivalent radical of formula (a) or (b) and $R^1$ is $C_{1-6}$ alkyl substituted with $Ar^1$.

Particularly preferred compounds of formula (I) to be used as active ingredient in the compositions of the present invention are those wherein $A^1=A^2-A^3=A^4$ is a bivalent radical of formula (a) or (b), R is hydrogen, $R^2$ is hydrogen or $C_{1-6}$ alkyl and $R^1$ is $C_{1-6}$ alkyl substituted with a member selected from the group consisting of phenyl being optionally substituted with up to two substituents independently selected from the group consisting of halo, hydroxy, and $C_{1-6}$ alkyl; pyridyl; imidazolyl; thienyl; halothienyl; furanyl; $C_{1-6}$ alkyl substituted furanyl; thiazolyl and pyrazinyl; whereby $R^1$ being furanylmethyl or $(C_{1-6}$ alkyl)furanylmethyl is especially preferred.

The most preferred compound of formula (I) to be used as active ingredient in the compositions of the present invention is 3-[(5-methyl-2-furanyl)methyl]-N-(4-piperidinyl)-3H-imidazo[4,5-b]pyridin-2-amine or a pharmaceutically acceptable acid addition salt thereof.

The compounds of formula (I) as well as their preparation are known and are described in, for example, U.S. Pat. Nos. 4,219,559 and 4,556,660.

Beside the methods described in these patents, the compounds of formula (I) can also be prepared by a number of novel processes, said novel processes constituting a further aspect of the present invention.

The compounds of formula (I) can be prepared by reacting a piperidine derivative of formula (II) with a benzimidazole derivative of formula (III) optionally followed by a decarboxylation reaction.

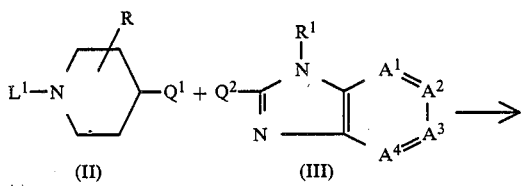

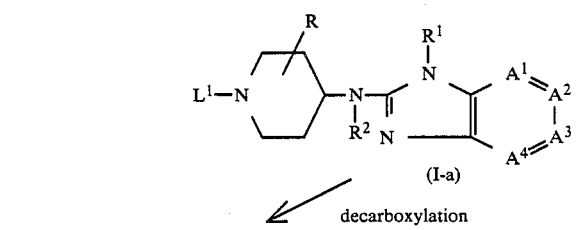

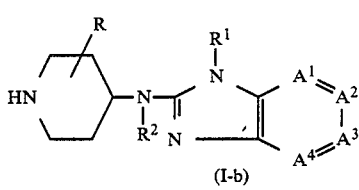

In (II) and (I-a) $L^1$ has the same meaning of L provided that it is not hydrogen, while $Q^1$ and $Q^2$ in (II), respectively (III) are selected so that during the reaction of (II) with (III) the $-NR^2-$ moiety is formed connecting the piperidine and benzimidazole moiety. For example $Q^1$ may be a radical $-NHR^2$ and $Q^2$ a radical $-W$ or inversely $Q^1$ may be a radical $-W'$ and $Q^2$ a radical $-NHR^2$

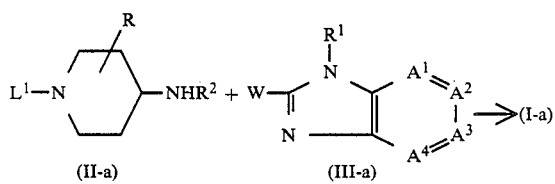

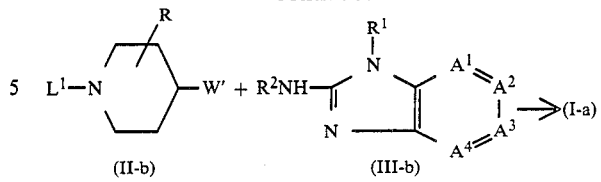

In (III-a) and (II-b) W and W' respresent an appropriate leaving group such as, for example, halo, e.g., chloro, bromo or iodo, or a sulfonyloxy group, e.g. methylsulfonyloxy or 4-methylphenylsulfonyloxy, whereas W may also be alkyloxy or alkylthio. The reaction of (II-a) with (III-a) and of (II-b) with (III-b) are conveniently conducted in an inert organic solvent such as, for example, an aromatic hydrocarbon, e.g., benzene, methylbenzene, dimethylbenzene, and the like; a lower alkanol, e.g., methanol, ethanol, 1-butanol and the like; a ketone, e.g., 2-propanone, 4-methyl-2-pentanone and the like; an ether, e.g., 1,4-dioxane, 1,1'-oxybisethane, tetrahydrofuran and the like; N,N-dimethylformamide (DMF); N,N-dimethylacetamide (DMA); nitrobenzene; dimethyl sulfoxide (DMSO); 1-methyl-2-pyrrolidinone; and the like. The addition of an appropriate base such as, for example, an alkali metal carbonate or hydrogen carbonate, sodium hydride or an organic base such as, for example, N,N-diethylethanamine or N-(1-methylethyl)-2-propanamine may be utilized to pick up the acid which is liberated during the course of the reaction. In some circumstances the addition of a iodide salt, preferably an alkali metal iodide, is appropriate. Somewhat elevated temperatures may enhance the rate of the reaction. Or, $Q^1$ may be an oxo radical and $Q^2$ a radical $-NRH^2$.

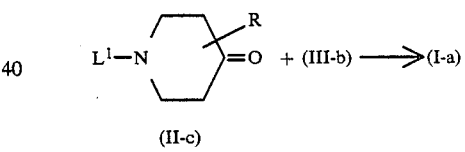

The reaction of (II-c) with (III-b) is conveniently carried out by treating a mixture of the reactants in a suitable reaction-inert organic solvent with an appropriate reductant. The reaction mixture may be stirred and/or heated in order to enhance the reaction rate. Preferably, the piperidone of formula (II-c) is first reacted with the benzimidazoleamine of formula (III-b) to form an enamine, which optionally may be isolated and further purified, and subsequently subjecting the said enamine to a reduction reaction. Suitable solvents are, for example, water; $C_{1-6}$ alkanols, e.g. methanol, ethanol, 2-propanol and the like; cyclic ethers, e.g. 1,4-dioxane and the like; halogenated hydrocarbons e.g. trichloromethane and the like; N,N-dimethylformamide; N,N-dimethylacetamide; dimethyl sulfoxide and the like; or a mixture of such solvents. Appropriate reductants are for example, metal or complex metal hydrides, e.g. sodium borohydride, lithium aluminiumhydride; or hydrogen, the latter being preferably used in the presence of a suitable catalyst such as, for example, palladium-on-charcoal, platinum-on-charcoal and the like. In order to prevent the undesired further hydrogenation of certain functional groups in the reactants and the reaction products it may be advantageous to add an appropriate catalyst-poison to the reaction mixture, e.g., thiophene and the like.

The decarboxylation reaction of (I-a) to prepare the piperidine compounds of formula (I-b) may be performed by treating the starting compound of formula (I-a) with an acid or a base in a suitable solvent. As suitable acids or bases there may be cited hydrohalic acids, e.g. hydrochloric acid or hydrobromic acid, sulfuric, phosphoric and the like acids preferably employed as an aqueous solution or mixed with e.g. acetic acid. Suitable bases are the alkalimetal hydroxides, hydrides or alkoxides in an aqueous or alcoholic medium.

In all of the foregoing and in the following preparations, the reaction products may be isolated from the reaction mixture and, if necessary, further purified according to methodologies generally known in the art.

The compounds of formula (I) have basic properties and, consequently, they may be converted to their therapeutically active non-toxic acid addition salt forms by treatment with appropriate acids, such as, for example, inorganic acids, such as hydrohalic acid, e.g. hydrochloric, hydrobromic and the like, and sulfuric acid, nitric acid, phosphoric acid and the like; or organic acids, such as, for example, acetic, propanoic, hydroxyacetic, 2-hydroxypropanoic, 2-oxopropanoic, ethanedioic, propanedioic, butanedioic, (Z)-2-butenedioic, (E)-2-butenedioic, 2-hydroxybutanedioic, 2,3-dihydroxybutanedioic, 2-hydroxy-1,2,3-propanetricarboxylic, methanesulfonic, ethanesulfonic, benzenesulfonic, 4-methylbenzenesulfonic, cyclohexanesulfamic, 2-hydroxybenzoic, 4-amino-2-hydroxybenzoic and the like acids.

Conversely the salt form can be converted by treatment with alkali into the free base form.

The intermediates and starting materials in the foregoing preparations are known compounds which may be prepared according to art-known methodologies of preparing said or similar compounds.

From formula (I) it is evident that the compounds of this invention may have several asymmetric carbon atoms in their structure. Each of these chiral centers may be present in a R- and a S-configuration, this R- and S-notation being in correspondence with the rules described by R. S. Cahn, C. Ingold and V. Prelog in Angew. Chem., Int. Ed. Engl., 5, 385, 511 (1966).

Pure stereochemically isomeric forms of the compounds of formula (I) may be obtained by the application of art-known procedures. Diastereoisomers may be separated by physical separation methods such as selective crystallization and chromatographic techniques, e.g., counter current distribution, and enantiomers may be separated from each other by the selective crystallization of their diastereomeric salts with optically active acids.

Pure stereochemically isomeric forms may also be derived from the corresponding pure stereochemically isomeric forms of the appropriate starting materials, provided that the reaction occurs stereospecifically.

It is evident that the cis and trans diastereomeric racemates may be further resolved into their optical isomers, cis(+), cis(−), trans(+) and trans(−) by the application of methodologies known to those skilled in the art.

Stereochemically isomeric forms of the compounds of formula (I) are naturally intended to be embraced within the scope of the invention.

An additional feature of the present invention comprises the fact that those compounds of formula (I) wherein $R^1$ is $C_{1-6}$alkyl substituted with $C_{1-6}$alkyl-substituted furanyl and wherein said $C_{1-6}$alkyl-substituted furanyl is other than 5-methyl-2-furanyl, said compounds being represented by the formula

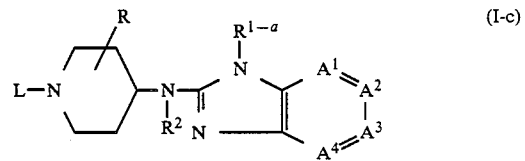

(I-c)

and the pharmaceutically acceptable acid addition salts and the stereochemically isomeric forms thereof are novel compounds.

Preferred novel compounds are those compounds of formula (I-c) wherein $R^{1-a}$ is $C_{1-6}$ alkyl substituted with 3- or 4-($C_{1-6}$alkyl)-2-furanyl or with 2-($C_{1-6}$alkyl)-3-furanyl.

Particularly preferred novel compounds are those preferred novel compounds wherein $R^{1-a}$ is methyl substituted with 3-($C_{1-6}$alkyl)-2-furanyl, $R^2$ is hydrogen, R is hydrogen and $A^1=A^2-A^3=A^4$ is CH=CH—CH=CH or N=CH—CH=CH.

Some of the compounds of formula (I) which can be used as active ingredient in the compositions and methods of treatment according to the present invention are listed in the following tables with the purpose of illustrating the invention and not to limiting it thereto.

TABLE I

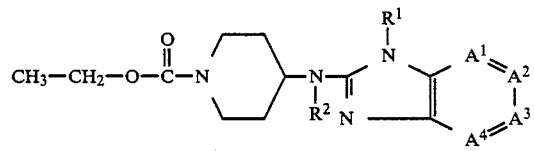

| comp. no. | $R^1$ | $R^2$ | $A^1=A^2-A^3=A^4$ | Salt/base | mp. (°C.) |
|---|---|---|---|---|---|
| 1 | H | H | —CH=CH—C(Cl)=CH— | base | 234.1 |
| 2 | H | H | —CH=CH—CH=CH— | base | — |
| 3 | H | H | —CH=CH—C(CH$_3$)=CH— | base | — |
| 4 | CH$_3$ | H | —CH=CH—C(CH$_3$)=CH— or —CH=C(CH$_3$)—CH=CH— | base | 142 |
| 5 | CH$_3$ | H | —CH=CH—CH=CH— | base | 166.7 |
| 6 | C$_2$H$_5$ | H | —CH=CH—CH=CH— | base | — |
| 7 | C$_3$H$_7$—n | H | —CH=CH—CH=CH— | base | — |
| 8 | C$_6$H$_5$—CH$_2$ | H | —CH=CH—CH=CH— | base | — |
| 9 | C$_5$H$_{11}$—n | H | —CH=CH—CH=CH— | base | — |

TABLE I-continued $$CH_3-CH_2-O-\underset{\underset{O}{\|}}{C}-N\diagdown\text{piperidine}\diagdown N(R^2)-C(=N-)-N(R^1)-\text{Ar}(A^1=A^2-A^3=A^4)$$

| comp. no. | R¹ | R² | A¹=A²—A³=A⁴ | Salt/base | mp. (°C.) |
|---|---|---|---|---|---|
| 10 | $C_7H_{15}$—n | H | —CH=CH—CH=CH— | base | — |
| 11 | $C_4H_9$—n | H | —CH=CH—CH=CH— | base | — |
| 12 | $C_6H_{13}$—n | H | —CH=CH—CH=CH— | base | — |
| 13 | cyclopentyl | H | —CH=CH—CH=CH— | base | — |
| 14 | $C_3H_7$—i | H | —CH=CH—CH=CH— | base | — |
| 15 | H | $CH_3$ | —CH=CH—CH=CH— | base | — |
| 16 | $C_6H_5$—$CH_2$ | $CH_3$ | —CH=CH—CH=CH— | HCl | 258 |
| 17 | 4-Cl—$C_6H_4$—$CH_2$ | H | —CH=CH—CH=CH— | base | 202.6 |
| 18 | 2-Cl—$C_6H_4$—$CH_2$ | H | —CH=CH—CH=CH— | base | 213.4 |
| 19 | 4-$CH_3$—$C_6H_4$—$CH_2$ | H | —CH=CH—CH=CH— | base | 177.7 |
| 20 | 4-Br—$C_6H_4$—$CH_2$ | H | —CH=CH—CH=CH— | base | — |
| 21 | 4-F—$C_6H_4$—$CH_2$ | H | —CH=CH—CH=CH— | base | 180.8 |
| 22 | H | $C_4H_9$—n | —CH=CH—CH=CH— | base | 225.9 |
| 23 | 2-F—$C_6H_4$—$CH_2$ | H | —CH=CH—CH=CH— | base | 176 |
| 24 | 4-F—$C_6H_4$—$CH_2$ | H | —CH=CH—C($CH_3$)=CH— or —CH=C($CH_3$)—CH=CH— | base | 173.3 |
| 25 | $C_6H_5$—$CH_2$ | H | —CH=CH—C($CF_3$)=CH— | base | 200 |
| 26 | H | H | —CH=CH—C(F)=CH— | base | 227.5 |
| 27 | $C_6H_5$—$CH_2$ | H | —CH=CH—C(Cl)=CH— | base | 211.9 |
| 28 | $C_6H_5$—$CH_2$ | H | —N=CH—CH=CH— | base | 148.6 |
| 29 | $C_6H_5$—$CH_2$ | H | —CH=CH—C($CH_3$)=CH— or —CH=C($CH_3$)—CH=CH— | base | 179.3 |
| 30 | 4-F—$C_6H_4$—$CH_2$ | H | —N=CH—CH=CH— | base | 134.4 |
| 31 | H | H | —N=CH—CH=CH— | base | 216.1 |
| 32 | 4-F—$C_6H_4$—$CH_2$ | H | —CH=CH—C(Cl)=CH— | base | 215.8 |
| 33 | $C_6H_5$ | H | —CH=CH—CH=CH— | base | 137 |
| 34 | 4-F—$C_6H_4$—$CH_2$ | H | —CH=CH—C(F)=CH— or —CH=C(F)—CH=CH— | base | 182.5 |
| 35 | $C_6H_5$—$CH_2$ | H | —CH=CH—C(F)=CH— or —CH=C(F)—CH=CH— | base | 184 |
| 36 | 4-F—$C_6H_5$ | H | —CH=CH—CH=CH— | base | 153 |
| 37 | 4-$NO_2$—$C_6H_4$—$CH_2$ | H | —CH=CH—CH=CH— | base | — |
| 38 | 2-$CH_3$, 4-F—$C_6H_3$—$CH_2$ | H | —CH=CH—CH=CH— | base | — |
| 39 | $C_6H_5$—$C_2H_4$ | H | —CH=CH—CH=CH— | $H_2O$ | 71.2 |
| 40 | 4-F—$C_6H_4$—$C_2H_4$ | H | —CH=CH—CH=CH— | ethanolate (1:1) | 110.2 |
| 41 | 3-F—$C_6H_4$—$CH_2$ | H | —CH=CH—CH=CH— | base | 184.6 |
| 42 | H | H | —CH=CH—C($OCH_3$)=CH— | base | — |
| 43 | 4-F—$C_6H_4$—$CH_2$ | H | —CH=CH—C($OCH_3$)=CH— or —CH=C($OCH_3$)—CH=CH— | base | 169.8 / — |
| 44 | 2-pyridinyl-methyl | H | —CH=CH—CH=CH— | base | 161.5 |
| 45 | H | H | —CH=CH—N=CH— | 2HCl.½$H_2O$ | 206.3–209.1 |
| 46 | 3-pyridinyl-methyl | H | —CH=CH—CH=CH— | base | 191.4 |
| 47 | 5-$CH_3$—4-imidazolylmethyl | H | —CH=CH—CH=CH— | 2HCl | 233.7 |
| 48 | 2-pyrazinyl-methyl | H | —CH=CH—CH=CH— | 2HBr.$H_2O$ | 178.5–179.3 |
| 49 | 2-furanyl-methyl | H | —CH=CH—CH=CH— | base | 135.8 |
| 50 | 4-F—$C_6H_4$—$CH_2$ | H | —CH=CH—CH=N— | base | 212.5 |
| 51 | 4-F—$C_6H_4$—$CH_2$ | H | —CH=CH—N=CH— | 2HCl.$H_2O$ | — |
| 52 | 4-F—$C_6H_4$—$CH_2$ | H | —CH=N—CH=CH— | 2HCl.$H_2O$ | 168.6 |
| 53 | 2-pyridinyl-methyl | H | —N=CH—CH=CH— | base | 141.3 |
| 54 | H | H | —CH=C(F)—C(F)=CH— | base | 234.9 |
| 55 | 4-F—$C_6H_4$—$CH_2$ | H | —CH=C(F)—C(F)=CH— | base | 182.3 |
| 56 | 2-furanyl-methyl | H | —N=CH—CH=CH— | base | 149.2 |
| 57 | 4-F—$C_6H_4$—$CH_2$ | H | —CH=CH—C($OCH_3$)=CH— | base | — |
| 58 | 2-thienyl-methyl | H | —CH=CH—CH=CH— | base | 142.7 |
| 59 | 4-F—$C_6H_4$—$CH_2$ | H | —CH=C($OCH_3$)—CH=CH— | base | — |
| 60 | 3-furanyl-methyl | H | —CH=CH—CH=CH— | base | 150.7 |

TABLE I-continued

Structure: CH₃—CH₂—O—C(=O)—N(piperidine)—N(R²)—C(=N—)—N(R¹)— attached to ring with A¹=A²—A³=A⁴

| comp. no. | R¹ | R² | A¹=A²—A³=A⁴ | Salt/base | mp. (°C.) |
|---|---|---|---|---|---|
| 61 | 5-methyl-2-furanylmethyl | H | —CH=CH—CH=CH— | ½H₂O | 150.1 |
| 62 | 2-thienylmethyl | H | —N=CH—CH=CH— | base | — |
| 63 | 4-thiazolylmethyl | H | —CH=CH—CH=CH— | base | 156.2 |
| 64 | 4-CH₃O—C₆H₄—CH₂ | H | —CH=CH—CH=CH— | base | 157.1 |
| 65 | 4-F—C₆H₄—CH₂ | CH₃ | —CH=CH—CH=CH— | base | — |
| 66 | H | C₆H₅—CH₂ | —CH=CH—CH=CH— | base | — |
| 67 | 3-Cl—C₆H₄—CH₂ | H | —CH=CH—CH=CH— | base | — |
| 68 | 3,4-(CH₃)₂—C₆H₃—CH₂ | H | —CH=CH—CH=CH— | base | — |
| 69 | 2-CH₃—C₆H₄—CH₂ | H | —CH=CH—CH=CH— | base | — |
| 70 | 3-CH₃—C₆H₄—CH₂ | H | —CH=CH—CH=CH— | base | — |
| 71 | 2-Br, 4-F—C₆H₃—CH₂ | H | —CH=CH—CH=CH— | base | — |
| 72 | 2-I—C₆H₄—CH₂ | H | —CH=CH—CH=CH— | base | — |
| 73 | 4-CH₃OC(O)—C₆H₄—CH₂ | H | —CH=CH—CH=CH— | base | 151 |
| 74 | 4-F—C₆H₄—CH₂ | H | —CH=CH—C(CH₃)=CH— | base | 202 |
| 75 | 2,4-Cl₂—C₆H₃—CH₂ | H | —CH=CH—CH=CH— | base | — |
| 76 | 2,6-F₂—C₆H₃—CH₂ | H | —CH=CH—CH=CH— | base | 140 |
| 77 | 4-F—C₆H₄—CH₂ | C₆H₅—CH₂ | —CH=CH—CH=CH— | base | oil |
| 78 | cyclohexyl | H | —CH=CH—CH=CH— | base | — |
| 79 | 5-methyl-2-furanylmethyl | H | —N=CH—CH=CH— | base | — |
| 80 | 3-furanylmethyl | H | —N=CH—CH=CH— | base | 174.5 |
| 81 | 2-methyl-3-furanylmethyl | H | —N=CH—CH=CH— | base | 153.7 |
| 82 | 5-ethyl-2-furanylmethyl | H | —N=CH—CH=CH— | base | 111.1 |
| 83 | 2-methyl-3-furanylmethyl | H | —CH=CH—CH=CH— | base | 150.4 |
| 84 | 5-methyl-2-furanylmethyl | H | —CH=CH—N=CH— | base | 155.2 |
| 85 | 3-methyl-2-furanylmethyl | H | —N=CH—CH=CH— | base | — |
| 86 | 5-methyl-2-furanylmethyl | H | —CH=N—CH=CH— | base | — |
| 87 | 5-isopropyl-2-furanylmethyl | H | —N=CH—CH=CH— | base | — |
| 88 | 4-methyl-2-furanylmethyl | H | —N=CH—CH=CH— | base | — |

TABLE II

Structure: L'—O—C(=O)—N(piperidine with R substituent)—NH—C(=N—)—N(R¹)— attached to ring with A¹=A²—A³=A⁴

| comp. no. | L' | R¹ | R | A¹=A²—A³=A⁴ | Salt/base | mp. (°C.) |
|---|---|---|---|---|---|---|
| 89 | CH₃ | H | CH₃ | —CH=CH—CH=CH— | base | 155 |
| 90 | CH₃ | 4-F—C₆H₄—CH₂ | CH₃ | —CH=CH—CH=CH— | base | 172.5 |
| 91 | C₆H₅CH₂ | 4-F—C₆H₄—CH₂ | H | —N=CH—CH=CH— | base | 130 |
| 92* | CH₃ | C₆H₅—CH₂ | CH₃ | —CH=CH—CH=CH— | base | 191 |

*cis + trans isomer

TABLE III

| comp. no. | R¹ | R² | A¹=A²—A³=A⁴ | Salt/base | mp. (°C.) |
|---|---|---|---|---|---|
| 93 | H | H | —CH=CH—CH(Cl)=CH— | 2HBr | — |
| 94 | H | H | —CH=CH—CH=CH— | 2HBr | — |
| 95 | CH₃ | H | —CH=CH—C(CH₃)=CH— or —CH=C(CH₃)—CH=CH— | 2HBr | — |
| 96 | H | H | —CH=C(CH₃)—C=CH— | 2HBr | — |
| 97 | CH₃ | H | —CH=CH—CH=CH— | 2HBr | — |
| 98 | C₂H₅ | H | —CH=CH—CH=CH— | 2HBr.½H₂O | 334–338 |
| 99 | C₃H₇—n | H | —CH=CH—CH=CH— | 2HBr | — |
| 100 | C₆H₅—CH₂ | H | —CH=CH—CH=CH— | 2HBr | — |
| 101 | C₅H₁₁—n | H | —CH=CH—CH=CH— | base | — |
| 102 | C₇H₁₅—n | H | —CH=CH—CH=CH— | base | — |
| 103 | C₄H₉—n | H | —CH=CH—CH=CH— | base | — |
| 104 | C₆H₁₃—n | H | —CH=CH—CH=CH— | base | — |
| 105 | cyclopentyl | H | —CH=CH—CH=CH— | base | — |
| 106 | C₃H₇—i | H | —CH=CH—CH=CH— | base | — |
| 107 | H | CH₃ | —CH=CH—CH=CH— | 2HBr.H₂O | — |
| 108 | 2-Cl—C₆H₄—CH₂ | H | —CH=CH—CH=CH— | base | — |
| 109 | 4-Cl—C₆H₄—CH₂ | H | —CH=CH—CH=CH— | 2HBr.H₂O | — |
| 110 | 4-Br—C₆H₄—CH₂ | H | —CH=CH—CH=CH— | 2HBr.H₂O | >300 |
| 111 | 4-CH₃—C₆H₄—CH₂ | H | —CH=CH—CH=CH— | 2HBr | — |
| 112 | 4-F—C₆H₄—CH₂ | H | —CH=CH—CH=CH— | 2HBr | 290.2 |
| 113 | H | C₄H₉—n | —CH=CH—CH=CH— | 2HBr.H₂O | 223.1 |
| 114 | 2-F—C₆H₄—CH₂ | H | —CH=CH—CH=CH— | 2HBr | — |
| 115 | C₆H₅—CH₂ | H | —CH=CH—C(CF₃)=CH— | 2HBr | — |
| 116 | C₆H₅—CH₂ | H | —CH=CH—C(Cl)=CH— | 2HBr | >260 |
| 117 | C₆H₅—CH₂ | H | —N=CH—CH=CH— | 2HCl.H₂O | 298.1 |
| 118 | 4-F—C₆H₄—CH₂ | H | —CH=CH—C(Cl)=CH— | 2HBr | >260 |
| 119 | 4-F—C₆H₄—CH₂ | H | —CH=CH—C(CH₃)=CH— or —CH=C(CH₃)—CH=CH— | 2HBr | — |
| 120 | 4-F—C₆H₄—CH₂ | H | —CH=CH—C(F)=CH— or —CH=C(F)—CH=CH— | 2HBr | 285.6 |
| 121 | C₆H₅—CH₂ | H | —CH=CH—C(CH₃)=CH— or —CH=C(CH₃)—CH=CH— | 2HBr | — |
| 122 | C₆H₅—CH₂ | H | —CH=CH—C(F)=CH— or —CH=C(F)—CH=CH— | 2HBr | >260 |
| 123 | 4-F—C₆H₄—CH₂ | H | —N=CH—CH=CH— | 2HCl.H₂O | 269.7 |
| 124 | C₆H₅ | H | —CH=CH—CH=CH— | 2HBr.H₂O | >300 |
| 125 | 4-F—C₆H₅— | H | —CH=CH—CH=CH— | 2HBr | >300 |
| 126 | 4-NO₂—C₆H₄—CH₂ | H | —CH=CH—CH=CH— | 2HBr.H₂O | — |
| 127 | 2-CH₃, 4-F—C₆H₃—CH₂ | H | —CH=CH—CH=CH— | 2HBr | — |
| 128 | C₆H₅—C₂H₄ | H | —CH=CH—CH=CH— | base | 181.8 |
| 129 | 3-F—C₆H₄—CH₂ | H | —CH=CH—CH=CH— | base | 218.4 |
| 130 | 4-F—C₆H₄—CH₂ | H | —CH=CH—C(OH)=CH— or —CH=C(OH)—CH=CH— | 2HBr | — |
| 131 | 2-pyridinylmethyl | H | —CH=CH—CH=CH— | 3HBr | 295.9 |
| 132 | 3-pyridinylmethyl | H | —CH=CH—CH=CH— | 3HBr | >260 |
| 133 | 5-CH₃—4-imidazolylmethyl | H | —CH=CH—CH=CH— | 2HBr | 272.1 |
| 134 | 2-pyrazinylmethyl | H | —CH=CH—CH=CH— | 3HBr | — |
| 135 | 4-F—C₆H₄—CH₂ | H | —CH=CH—CH=N— | 2HBr | >300.6 |
| 136 | 2-furanylmethyl | H | —CH=CH—CH=CH— | base | 211.0 |
| 137 | 4-F—C₆H₄—CH₂ | H | —CH=CH—CH=CH— | base | 215.5 |
| 138 | 4-F—C₆H₄—CH₂ | H | —CH=CH—N=CH— | 2HBr | 279.4 |
| 139 | 2-pyridinylmethyl | H | —N=CH—CH=CH— | 3HBr | 265.5 |
| 140 | 2-furanylmethyl | H | —N=CH—CH=CH— | base | 159.0 |
| 141 | 4-F—C₆H₄—CH₂ | H | —CH=N—CH=CH— | 2HBr.H₂O | 291.6 |
| 142 | 4-F—C₆H₄—CH₂ | H | —CH=C(F)—C(F)=CH— | 2HBr | 210.6 |
| 143 | 4-F—C₆H₄—CH₂ | H | —CH=CH—C(OH)=CH— | 2HBr | — |
| 144 | 2-thienylmethyl | H | —CH=CH—CH=CH— | base | — |

TABLE III-continued

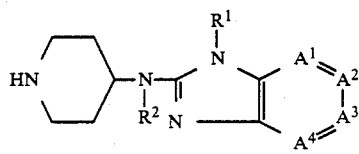

| comp. no. | R¹ | R² | A¹=A²—A³=A⁴ | Salt/base | mp. (°C.) |
|---|---|---|---|---|---|
| 145 | 4-F—C₆H₄—CH₂ | H | —CH=C(OH)—CH=CH— | 2HBr | — |
| 146 | 3-furanyl-methyl | H | —CH=CH—CH=CH— | base | — |
| 147 | 5-methyl-2-furanylmethyl | H | —CH=CH—CH=CH— | base | — |
| 148 | 2-thienyl-methyl | H | —N=CH—CH=CH— | base | 189.6 193.5 |
| 149 | 4-thiazolyl methyl | H | —CH=CH—CH=CH— | 2HBr.2H₂O | 223.5 |
| 150 | 4-CH₃O—C₆H₄—CH₂ | H | —CH=CH—CH=CH— | base | 178.1 |
| 151 | 4-F—C₆H₄—CH₂ | H | —CH=CH—C(OCH₃)=CH— | base | — |
| 152 | 4-F—C₆H₄—CH₂ | CH₃ | —CH=CH—CH=CH— | 2HCl.H₂O | 222.2 |
| 153 | 4-F—C₆H₄—CH₂ | H | —CH=C(OCH₃)—CH=CH— | base | — |
| 154 | H | C₆H₅—CH₂ | —CH=CH—CH=CH— | base | — |
| 155 | 3-Cl—C₆H₄—CH₂ | H | —CH=CH—CH=CH— | 2HBr | 262.2 |
| 156 | 3,4-(CH₃)₂—C₆H₃—CH₂ | H | —CH=CH—CH=CH— | 2HBr | — |
| 157 | 2-CH₃—C₆H₄—CH₂ | H | —CH=CH—CH=CH— | 2HBr | — |
| 158 | 3-CH₃—C₆H₄—CH₂ | H | —CH=CH—CH=CH— | 2HBr | — |
| 159 | 2-Br,4-F—C₆H₃—CH₂ | H | —CH=CH—CH=CH— | 2HBr | — |
| 160 | 2-I—C₆H₄—CH₂ | H | —CH=CH—CH=CH— | 2HBr.2H₂O | 265.2 |
| 161 | 4-F—C₆H₄—CH₂ | H | —CH=CH—C(CH₃)=CH— | base | — |
| 162 | 2,4-Cl₂—C₆H₃—CH₂ | H | —CH=CH—CH=CH— | 2HBr | 225.6 |
| 163 | 2,6-F₂—C₆H₃—CH₂ | H | —CH=CH—CH=CH— | 2HBr | 295.5 |
| 164 | 4-F—C₆H₄—CH₂ | C₆H₅—CH₂ | —CH=CH—CH=CH— | base | — |
| 165 | cyclohexyl | H | —CH=CH—CH=CH— | base | 180 |
| 166 | 5-methyl-2-furanylmethyl | H | —N=CH—CH=CH— | base | 119.8 |
| 167 | 3-furanyl-methyl | H | —N=CH—CH=CH— | base | 145 |
| 168 | 2-furanyl-methyl | H | —N=CH—CH=CH— | (Z)-2-but-enedioate (1:2) | 170.0 |
| 169 | 2-furanyl-methyl | H | —N=CH—CH=CH— | 2HCl.½H₂O | 200.9 |
| 170 | 2-furanyl-methyl | H | —N=CH—CH=CH— | * | 131.5 |
| 171 | 3-furanyl-methyl | H | —N=CH—CH=CH— | 2HCl.½H₂O | 278.7 |
| 172 | H | H | —N=CH—CH=CH— | 2HBr | 295.1 |
| 173 | 2-methyl-3-furanylmethyl | H | —N=CH—CH=CH— | base | 164.7 |
| 174 | 5-ethyl-2-furanylmethyl | H | —N=CH—CH=CH— | base | 106.1 |
| 175 | 5-methyl-2-furanylmethyl | H | —CH=CH—N=CH— | base | 185.6 |
| 176 | 2-methyl-3-furanylmethyl | H | —CH=CH—CH=CH— | base | 168.0 |
| 177 | 3-methyl-2-furanylmethyl | H | —N=CH—CH=CH— | base | 160.3 |
| 178 | 5-methyl-2-furanylmethyl | H | —CH=N—CH=CH— | ½H₂O | 146.2 |
| 179 | 5-methyl-2-furanylmethyl | H | —N=CH—CH=CH— | 2HCl.½H₂O | 204.1 |
| 180 | 5-methyl-2-furanylmethyl | H | —N=CH—CH=CH— | 2HNO₃ | 170.5 |
| 181 | 5-methyl-2-furanylmethyl | H | —N=CH—CH=CH— | (Z)-2-but-enedioate (1:2) | 154.5 |
| 182 | 5-isopropyl-2-furanylmethyl | H | —N=CH—CH=CH— | | |
| 183 | 4-methyl-2-furanylmethyl | H | —N=CH—CH=CH— | | |

*(+)-[R—(R*,R*)]-2,3-dihydroxybutanedioate (2:3)

TABLE IV

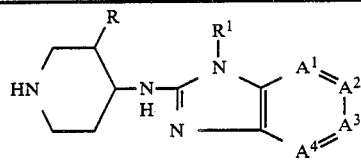

| comp. no. | R¹ | R | A¹=A²—A³=A⁴ | Salt/base | mp. (°C.) |
|---|---|---|---|---|---|
| 184 | 4-F—$C_6H_4$—$CH_2$ | $CH_3$ | —CH=CH—CH=CH— | 2HBr | — |
| 185 | $C_6H_5$—$CH_2$ | $CH_3$ | —CH=CH—CH=CH— | 2HBr.$H_2O$ | 250.2 |

The use of the compounds of formula (I), the pharmaceutically acceptable acid-addition salts and possible stereochemically isomeric forms thereof in the compositions of the present invention is based on their useful pharmacological properties. More particularly, they are active as anti-histaminics which activity is clearly evidenced by the results obtained in the "Protection of Rats from Compound 48/80-induced lethality"-test. In addition thereto, they are also devoid of sedating effects which is an undesirable side-effect often encountered with anti-histaminics. Apart from their anti-histaminic properties they also show serotonin-antagonism.

Furthermore, the compounds of formula (I), the pharmaceutically acceptable acid-addition salts and stereochemically isomeric forms thereof are particularly attractive due to their favourable pharmacokinetical profile. On the one hand they show a rapid onset so that their anti-histaminic effects are almost instantaneously present. On the other hand they possess an attractive duration of effect, i.e., while being not too short, thus avoiding the necessity of frequent administrations, said duration is not too long either. Hence, the dose regimen can suitably be adapted to the evolution of the symptoms.

To prepare the pharmaceutical compositions of this invention, an effective amount of the particular compound, in base or acid-addition salt form, as the active ingredient is combined in intimate admixture with a pharmaceutically acceptable carrier, which carrier may take a wide variety of forms depending on the form of preparation desired for administration. These pharmaceutical compositions are desirably in unitary dosage form suitable, preferably, for administration orally, rectally, percutaneously, or by parenteral injection. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions: or solid carriers such as starches, sugars, kaolin, lubricants, binders, disintegrating agents and the like in the case of powders, pills, capsules and tablets. Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. In the compositions suitable for percutaneous administration, the carrier optionally comprises a penetration enhancing agent and/or a suitable wettable agent, optionally combined with suitable additives of any nature in minor proportions, which additives do not introduce a significant deleterious effect on the skin. Said additives may facilitate the administration to the skin and/or may be helpful for preparing the desired compositions. These compositions may be administered in various ways, e.g., as a transdermal patch, as a spot-on, as an ointment. Acid addition salts of (I) due to their increased water solubility over the corresponding base form, are obviously more suitable in the preparation of aqueous compositions. It is especially advantageous to formulate the aforementioned pharmaceutical compositions in dosage unit form for each of administration and uniformity of dosage. Dosage unit form as used in the specification and claims herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoon-fuls and the like, and segregated multiples thereof.

In a further aspect of the present invention there is provided a method of treating allergic diseases in warm-blooded animals suffering from said allergic diseases, which method comprises the administration to said warm-blooded animals of an effective anti-allergic amount of a compound of formula (I) a pharmaceutically acceptable acid-addition salt or possible stereochemically isomeric form thereof. Preferably said effective amount of the active ingredient is administered as a composition as described hereinabove. Those of skill in the pertinent art could easily determine the effective anti-allergic amount from the test results presented here. In general it is contemplated that an effective amount would be from 0.001 mg/kg to 100 mg/kg body weight, and more preferably from 0.01 mg/kg to 1 mg/kg body weight.

EXAMPLES (A) Preparation of Intermediates

Example 1

A mixture of 47.5 parts of $N^2$-(2-furanylmethyl)-2,3-pyridinediamine, 36.5 parts of methyl (α-imino-α-methoxymethyl)carbamate, 34.5 parts of acetic acid and 450 parts of methylbenzene was stirred and heated for 16 hours at 65°–68° C. The reaction mixture was evaporated. 140 Parts of potassium hydroxide, 50 parts of water and 400 parts of 2-propanol were added to the residue and stirring was continued for 16 hours at reflux. The reaction mixture was concentrated to ¼ of its volume. 500 Parts of water were added and 2-propanol was distilled off azeotropically. After stirring for 1 hour at room temperature, the product was filtered off, washed successively twice with 20 parts of water and three times with 12 parts of 2-propanone and crystallized from 1,2-dichloroethane. The produce was filtered off and dried in vacuo at 50° C., yielding 27.3 parts (51.0%) of 3-(2-furanylmethyl)-3H-imidazo[4,5-b]pyridin-2-amine; mp. 193.3° C.

(B) Preparation of Final Compounds

Example 2

A mixture of 22.2 parts of ethyl 4-oxo-1-piperidinecarboxylate, 21.4 parts of 3-(2-furanylmethyl)-3H-imidazo[4,5-b]pyridin-2-amine, 360 parts of methylbenzene and 0.1 parts of 4-methylbenzenesulfonic acid was stirred for 4 days at reflux temperature using a water separator. After cooling to 50° C., 64 parts of ethanol were added and 3.8 parts of sodium tetrahydroborate were added portionwise to the reaction mixture. Upon completion, stirring was continued for 2 hours at 50° C. After cooling, the mixture was decomposed with 3.5 parts of acetic acid. Water was added to the mixture while stirring and the layers were separated. The aqueous layer was extracted with methylbenzene. The combined methylbenzene layers were dried, filtered and evaporated, yielded ethyl 4-[[3-(2-furanylmethyl)-3H-imidazo[4,5-b]pyridin-2-yl]amino]-1-piperidinecarboxylate as an oily residue (compound 56).

Example 3

A mixture of ethyl 4-[[3-(2-furanylmethyl)-3H-imidazo[4,5-b]pyridin-2-yl]amino]-1-piperidinecarboxylate, 50 parts of potassium hydroxide, 400 parts of 2-propanol and 20 drops of water was stirred and refluxed for about 5 hours. The reaction mixture was evaporated and water was added to the residue. The product was extracted twice with 4-methyl-2-pentanone. The combined extracts were dried, filtered and evaporated. The solid residue was stirred in 1,1'-oxybisethane. The product was filtered off and dried, yielding 34 parts (85%) of 3-(2-furanylmethyl)-N-(4-piperidinyl)-3H-imidazo[4,5-b]pyridin-2-amine; mp. 159.0° C. (compound 140)

Example 4

A mixture of 9.8 parts of ethyl 4-amino-1-piperidinecarboxylate and 15 parts of 2-chloro-1-(4-fluorophenylmethyl)-1H-benzimidazole was heated to 120° C. The mixture was stirred at 120° C. during 43 hours. After cooling, 100 parts of trichloromethane were added and the whole was thouroughly stirred. The mixture was washed with water. The aqueous layer was separated and the organic mixture was filtered and evaporated. The collected solid material was dissolved in 100 parts of water and subsequently 100 parts of 20% sodium hydroxide solution were added. The precipitate was filtered and dried in vacuo at 50° C., yielding 12.1 parts (40.5%) of ethyl 4-[[1-[(4-fluorophenyl)methyl]-1H-benzimidazol-2-yl]amino]-1-piperidinecarboxylate; mp. 181° C. (compound 21).

Example 5

A mixture of 3.2 parts of ethyl 4-[1-[(4-fluorophenyl)methyl]-1H-benzimidazol-2-ylamino]-1-piperidinecarboxylate and 300 parts of hydrobromic acid solution 48% was stirred and refluxed for 1 hour. The reaction mixture was evaporated and the residue was crystallized from 2-propanol. The product was filtered off and dried, yielding 3.3 parts (82%) of 1-[(4-fluorophenyl)methyl]-N-(4-piperidinyl)-1H-benzimidazol-2-amine dihydrobromide; mp. 290.2° C. (compound 112).

All other compounds listed in Tables I to IV can be obtained by analogous methods of preparation.

(B) Pharmacological Examples

The useful anti-histaminic properties of the compounds of formula (I) which can be used as the active ingredient in the formulations according to the present invention can be demonstrated by the following test procedure.

Example 6

Protection of rats from compound 48/80-induced lethality

Compound 48/80, a mixture of oligomers obtained by condensation of 4-methoxy-N-methylbenzeneethanamine and formaldehyde has been described as a potent histamine releasing agent (Int. Arch. Allergy, 13, 336 (1958)). The protection from compound 48/80-induced lethal circulatory collapse appears to be a simple way of evaluating quantitatively the antihistaminic activity of test compounds. Male rats of an inbred Wistar strain, weighing 240–260 g were used in the experiment. After overnight starvation the rats were transferred to conditioned laboratories (temp.=21±1° C., relative humidity=65±5%). The rats were treated subcutaneously or orally with a test compound or with the solvent (NaCl solution, 0.9%). One hour after treatment there was injected intravenously compound 48/80, freshly dissolved in water, at a dose of 0.5 mg/kg (0.2 ml/100 g of body weight). In control experiments, wherein 250 solvent-treated animals were injected with the standard dose of compound 48/80, not more than 2.8% of the animals survived after 4 hours. Survival after 4 hours is therefore considered to be a safe criterion of a protective effect of drug administration. The $ED_{50}$-values of the compounds of formula (I) are listed in table 1. Said $ED_{50}$-values are the values in mg/kg body weight at which the tested compounds protect 50% of the tested animals against compound 48/80-induced lethality.

TABLE I

| No. | compound 48/80 lethality test in rats-$ED_{50}$ in mg/kg body weight |
|---|---|
| 112 | 0.056 |
| 123 | 0.08 |
| 135 | 0.01 |
| 140 | 0.08 |
| 166 | 0.04 |

(C) Composition Examples

The following formulations exemplify typical pharmaceutical compositions in dosage unit form suitable for systemic administration to animal and human subjects in accordance with the present invention. These examples are given to illustrate and not to limit the scope of the present invention.

Example 7: Oral Drops 500 g of 3-(2-furanylmethyl)-N-(4-piperidinyl)-3H-imidazo[4,5-b]pyridin-2-amine was dissolved in 0.5 l of 2-hydroxypropanoic acid and 1.5 l of the polyethylene glycol at 60°–80° C. After cooling to 30°–40° C. there were added 35 l of polyethylene glycol and the mixture was stirred well. Then there was added a solution of 1750 g of sodium saccharin in 2.5 l of purified water and while stirring there were added 2.5 l of cocoa flavor and polyethylene glycol q.s. to a volume of 50 l, providing an oral drop solution comprising 10 mg of the 3-(2-furanylmethyl)-N-(4-piperidinyl)-3H-imidazo[4,5-b]pyridin-2-amine per ml. The resulting solution was filled into suitable containers.

Example 8: Oral Solution 9 g of methyl 4-hydroxybenzoate and 1 g of propyl 4-hydroxybenzoate were dissolved in 4 l of boiling purified water. In 3 l of this solution were dissolved first 10 g of 2,3-dihydroxybutanedioic acid and thereafter 20 g of the 3-[(5-methyl-2-furanyl)methyl]-N-(4-piperidinyl)-3H-imidazo[4,5-b]pyridin-2-amine. The latter solution was combined with the remaining part of the former solution and 12 l 1,2,3-propanetriol and 3 l of sorbitol 70% solution were added thereto. 40 g of sodium saccharin were dissolved in 0.5 l of water and a 2 ml of raspberry and 2 ml of gooseberry essence were added. The latter solution was combined with the former, water was added q.s. to a volume of 20 l providing an oral solution comprising 20 mg of 3-[(5-methyl-2-furanyl)methyl]-N-(4-piperidinyl-3H-imidazo[4,5-b]pyridin-2-amine per teaspoonful (5 ml). The resulting solution was filled in suitable containers.

Example 9: Capsules 20 g of 3-(2-furanylmethyl)-N-(4-piperidinyl)-3H-imidazo[4,5-b]pyridin-2-amine, 6 g sodium lauryl sulfate, 56 g starch, 56 g lactose, 0.8 g colloidal silicon dioxide, and 1.2 g magnesium stearate were vigorously stirred together. The resulting mixture was subsequently filled into 1000 suitable hardened gelating capsules, comprising each 20 mg of 3-(2-furanylmethyl)-N-(4-piperidinyl)-3H-imidazo[4,5-b]-pyridin-2-amine.

Example 10: Film-Coated Tablets

Preparation of tablet core

A mixture of 100 g of 3-[(5-methyl-2-furanyl)methyl]-N-(4-piperidinyl)-3H-imidazo[4,5-b]pyridin-2-amine, 570 g lactose and 200 g starch was mixed well and thereafter humidified with a solution of 5 g sodium dodecyl sulfate and 10 g polyvinylpyrrolidone in about 200 ml of water. The wet powder mixture was sieved, dried and sieved again. Then there was added 100 g microcrystalline cellulose and 15 g hydrogenated vegetable oil. The whole was mixed well and compressed into tablets, giving 10.000 tablets, each containing 10 mg of 3-[(5-methyl-2-furanyl)methyl]-N-(4-piperidinyl)-3H-imidazo[4,5-b]pyridin-2-amine.

Coating

To a solution of 10 g methyl cellulose in 75 ml of denaturated ethanol there was added a solution of 5 g of ethyl cellulose in 150 ml of dichloromethane. Then there were added 75 ml of dichloromethane and 2.5 ml 1,2,3-propanetriol. 10 g of polyethylene glycol was molten and dissolved in 75 ml of dichloromethane. The latter solution was added to the former and then there were added 2.5 g of magnesium octadecanoate, 5 g of polyvinylpyrrolidone and 30 ml of concentrated colour suspension (Opaspray K-1-2109 ®) and the whole was homogenated.

The tablet cores were coated with the thus obtained mixture in a coating apparatus.

Example 11: Injectable Solution 1.8 g methyl 4-hydroxybenzoate and 0.2 g propyl 4-hydroxy-benzoate were dissolved in about 0.5 l of boiling water for injection. After cooling to about 50° C. there were added while stirring 4 g lactic acid, 0.05 propylene glycol and 4 g of 3-(2-furanylmethyl)-N-(4-piperidinyl)-3H-imidazo[4,5-b]pyridin-2-amine. The solution was cooled to room temperature and supplemented with water for injection q.s. ad 1 l volume, giving a solution of 4 mg 3-(2-furanylmethyl)-N-(4-piperidinyl)-3H-imidazo[4,5-b]pyridin-2-amine per ml. The solution was sterilized by filtration (U.S.P. XVII p. 811) and filled in sterile containers.

Example 12: Suppositories 3 g 3-[(5-methyl-2-furanyl)methyl]-N-(4-piperidinyl)-3H-imidazo[4,5-b]pyridin-2-amine was dissolved in a solution of 3 g 2,3-dihydroxybutanedioic acid in 25 ml polyethylene glycol 400. 12 g surfactant and triglycerides q.s. ad 300 g were molten together. The latter mixture was mixed well with the former solution. The thus obtained mixture was poured onto moulds at a temperature of 37°–38° C. to form 100 suppositories each containing 30 mg of 3-[(5-methyl-2-furanyl)methyl]-N-(4-piperidinyl)-3H-imidazo[4,5-b]pyridin-2-amine.

What we claim is:

1. An anti-allergic composition comprising one or more pharmaceutical carriers and as active ingredient an anti-allergic effective amount of at least one compound having the formula

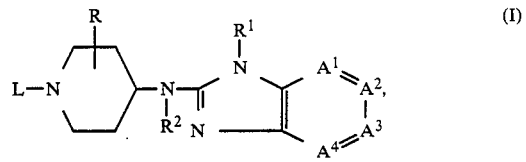

a pharmaceutically acceptable acid addition salt or a possible stereochemically isomeric form thereof, wherein:

L is hydrogen, $C_{1-6}$ alkyloxycarbonyl or phenylmethoxycarbonyl;

$A^1=A^2-A^3=A^4$ is a bivalent radical having the formula

| | |
|---|---|
| $-CH=CH-CH=CH-$ | (a), |
| $-N=CH-CH=CH-$ | (b), |
| $-CH=N-CH=CH-$ | (c), |
| $-CH=CH-N=CH-$ | (d), |
| or | |
| $-CH=CH-CH=N-$ | (e), | wherein one or two hydrogen atoms in said radicals (a)–(e) may, each independently from each other, be replaced by halo, $C_{1-6}$ alkyl, $C_{1-6}$ alkyloxy, trifluoromethyl or hydroxy;

R is a member selected from the group consisting of hydrogen and $C_{1-6}$ alkyl;

R¹ is a member selected from the group consisting of hydrogen, $C_{1-10}$ alkyl, $C_{3-6}$ cycloalkyl, $Ar^1$ and $C_{1-6}$ alkyl substituted with one or two $Ar^1$ radicals;

R² is a member selected from the group consisting of hydrogen, $C_{1-6}$ alkyl, $C_{3-6}$ cycloalkyl, ($C_{1-6}$alkyl)—CO—, ($C_{1-6}$alkyloxy)—CO and $Ar^2$-$C_{1-6}$ alkyl;

wherein $Ar^1$ is a member selected from the group consisting of phenyl, being optionally substituted with up to three substituents each independently selected from the group consisting of halo, hydroxy, nitro, cyano, trifluoromethyl, $C_{1-6}$ alkyl, $C_{1-6}$ alkyloxy, $C_{1-6}$ alkylthio, mercapto, amino, mono- and di($C_{1-6}$ alkyl)amino, carboxyl, $C_{1-6}$ alkyloxycarbonyl and $C_{1-6}$ alkyl—CO—; thienyl; halothienyl; furanyl; $C_{1-6}$ alkyl substituted furanyl; pyridinyl; pyrazinyl; thiazolyl and imidazolyl optionally substituted with $C_{1-6}$ alkyl; and wherein $Ar^2$ is a member selected from the group consisting of phenyl being optionally substituted with up to three substituents each independently selected from the group consisting of halo, hydroxy, nitro, cyano, trifluoromethyl, $C_{1-6}$ alkyl, $C_{1-6}$ alkyloxy, $C_{1-6}$ alkylthio, mercapto, amino, mono- and di($C_{1-6}$ alkyl)amino, carboxyl, $C_{1-6}$ alkyloxycarbonyl and ($C_{1-6}$ alkyl)—CO.

2. An anti-allergic composition according to claim 1 wherein $A^1=A^2-A^3=A^4$ is a bivalent radical of formula (a) or (b) and R¹ is $C_{1-6}$ alkyl substituted with $Ar^1$.

3. An anti-allergic composition according to claim 2 wherein R is hydrogen, R² is hydrogen or $C_{1-6}$ alkyl and $Ar^1$ is phenyl being optionally substituted with up to two substituents independently selected from the group consisting of halo, hydroxy, and $C_{1-6}$ alkyl; pyridyl; imidazolyl; thienyl; halothienyl; furanyl; $C_{1-6}$ alkyl substituted furanyl; thiazolyl and pyrazinyl.

4. An anti-allergic composition according to claim 3 wherein R¹ is furanylmethyl or ($C_{1-6}$ alkyl)furanylmethyl.

5. An anti-allergic composition according to claim 1 wherein the compound is 3-[(5-methyl-2-furanyl)methyl]-N-(4-piperidinyl)-3H-imidazo[4,5-b]pyridin-2-amine.

6. An anti-allergic composition according to claim 1 wherein L is hydrogen.

7. An anti-allergic composition according to claim 1 wherein L is other than hydrogen.

8. A method of treating allergic diseases in warm-blooded animals suffering from the same, which method comprises the systemic administration to warm-blooded animals of an effective anti-allergic amount of a compound having the formula

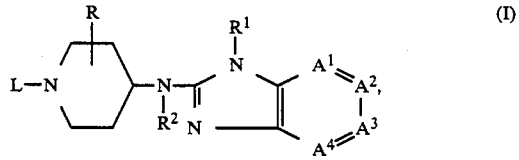

(I)

a pharmaceutically acceptable acid addition salt or a possible stereochemically isomeric form thereof, wherein:

L is hydrogen, $C_{1-6}$ alkyloxycarbonyl or phenylmethoxycarbonyl; $A^1=A^2-A^3=A^4$ is a bivalent radical having the formula —CH=CH—CH=CH—    (a), —N=CH—CH=CH—    (b), —CH=N—CH=CH—    (c), —CH=CH—N=CH—    (d), or —CH=CH—CH=N—    (e), wherein one or two hydrogen atoms in said radicals (a)–(e) may, each independently from each other, be replaced by halo, $C_{1-6}$ alkyl, $C_{1-6}$ alkyloxy, trifluoromethyl or hydroxy;

R is a member selected from the group consisting of hydrogen and $C_{1-6}$ alkyl;

R¹ is a member selected from the group consisting of hydrogen, $C_{1-10}$ alkyl, $C_{3-6}$ cycloalkyl, $Ar^1$ and $C_{1-6}$ alkyl substituted with one or two $Ar^1$ radicals;

R² is a member selected from the group consisting of hydrogen, $C_{1-6}$alkyl, $C_{3-6}$cycloalkyl, ($C_{1-6}$alkyl)—CO—, ($C_{1-6}$alkyloxy)—CO and $Ar^2$-$C_{1-6}$alkyl;

wherein $Ar^1$ is a member selected from the group consisting of phenyl, being optionally substituted with up to three substituents each independently selected from the group consisting of halo, hydroxy, nitro, cyano, trifluoromethyl, $C_{1-6}$ alkyl, $C_{1-6}$ alkyloxy, $C_{1-6}$ alkylthio, mercapto, amino, mono- and di($C_{1-6}$ alkyl)amino, carboxyl, $C_{1-6}$ alkyloxycarbonyl and $C_{1-6}$ alkyl—CO—; thienyl; halothienyl; furanyl; $C_{1-6}$ alkyl substituted furanyl; pyridinyl; pyrazinyl; thiazolyl and imidazolyl optionally substituted with $C_{1-6}$ alkyl; and wherein $Ar^2$ is a member selected from the group consisting of phenyl being optionally substituted with up to three substituents each independently selected from the group consisting of halo, hydroxy, nitro, cyano, trifluoromethyl, $C_{1-6}$ alkyl, $C_{1-6}$ alkyloxy, $C_{1-6}$ alkylthio, mercapto, amino, mono- and di($C_{1-6}$ alkyl)amino, carboxyl, $C_{1-6}$ alkyloxycarbonyl and ($C_{1-6}$ alkyl)—CO.

9. A method according to claim 8 wherein $A^1=A^2-A^3=A^4$ is a bivalent radical of formula (a) or (b) and R¹ is $C_{1-6}$ alkyl substituted with $Ar^1$.

10. A method according to claim 9 wherein R is hydrogen, R² is hydrogen or $C_{1-6}$ alkyl and $Ar^1$ is phenyl being optionally substituted with up to two substituents independently elected from the group consisting of halo, hydroxy, and $C_{1-6}$ alkyl; pyridyl; imidazolyl; thienyl; halothienyl; furanyl; $C_{1-6}$ alkyl substituted furanyl; thiazolyl and pyrazinyl.

11. A method according to claim 10 wherein R¹ is furanylmethyl or ($C_{1-6}$ alkyl)furanylmethyl.

12. A method according to claim 8 wherein the compound is 3-[(5-methyl-2-furanyl)methyl]-N-(4-piperidinyl)-3H-imidazo[4,5-b]pyridin-2-amine.

13. A method according to claim 8 wherein L is hydrogen.

14. A method according to claim 8 wherein L is other than hydrogen.

15. A chemical compound having the formula

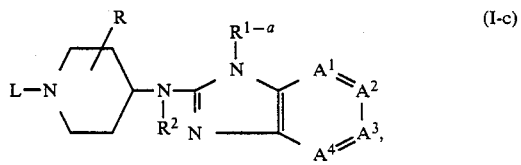

(I-c)

a pharmaceutically acceptable acid addition salt or a possible stereochemically isomeric form thereof, wherein:

L is hydrogen, $C_{1-6}$alkyloxycarbonyl or phenylmethoxycarbonyl;

$A^1=A^2-A^3=A^4$ is bivalent radical having the formula $$-CH=CH-CH=CH- \quad (a),$$

$$-N=CH-CH=CH- \quad (b),$$

$$-CH=N-CH=CH- \quad (c),$$

$$-CH=CH-N=CH- \quad (d);$$

or $$-CH=CH-CH=N- \quad (e),$$

wherein one or two hydrogen atoms in said radicals (a)-(e) may, each independently from each other, be replaced by halo, $C_{1-6}$ alkyl, $C_{1-6}$ alkyloxy, trifluoromethyl or hydroxy;

R is a member selected from the group consisting of hydrogen and $C_{1-6}$ alkyl;

$R^{1-a}$ is $C_{1-6}$alkyl substituted with $C_{1-6}$alkyl-substituted furanyl and wherein said $C_{1-6}$alkyl-substituted furanyl is other than 5-methyl-2-furanyl;

$R^2$ is a member selected from the group consisting of hydrogen, $C_{1-6}$ alkyl, $C_{3-6}$ cycloalkyl, ($C_{1-6}$ alkyl)—CO—, ($C_{1-6}$alkyloxy)—CO and $Ar^2$-$C_{1-6}$ alkyl; wherein $Ar^2$ is a member selected from the group consisting of phenyl being optionally substituted with up to three substituents each independently selected from the group consisting of halo, hydroxy, nitro, cyano, trifluoromethyl, $C_{1-6}$ alkyl, $C_{1-6}$ alkyloxy, $C_{1-6}$ alkylthio, mercapto, amino, mono- and di($C_{1-6}$ alkyl)amino, carboxyl, $C_{1-6}$ alkyloxycarbonyl and ($C_{1-6}$ alkyl)-CO.

16. A compound according to claim 15 wherein $R^{1-a}$ is $C_{1-6}$alkyl substituted with 3- or 4-($C_{1-6}$alkyl)-2-furanyl or with 2-($C_{1-6}$alkyl)-3-furanyl.

17. A compound according to claim 16 wherein $R^{1-a}$ is methyl substituted with 3-($C_{1-6}$alkyl)-2-furanyl, $R^2$ is hydrogen, R is hydrogen and $A^1=A^2-A^3=A^4$ is CH=CH—CH=CH or N=CH—CH=CH.

18. A chemical compound according to claim 15 wherein L is hydrogen.

19. A chemical compound according to claim 15 wherein L is other than hydrogen.

* * * * *